Figure 1:
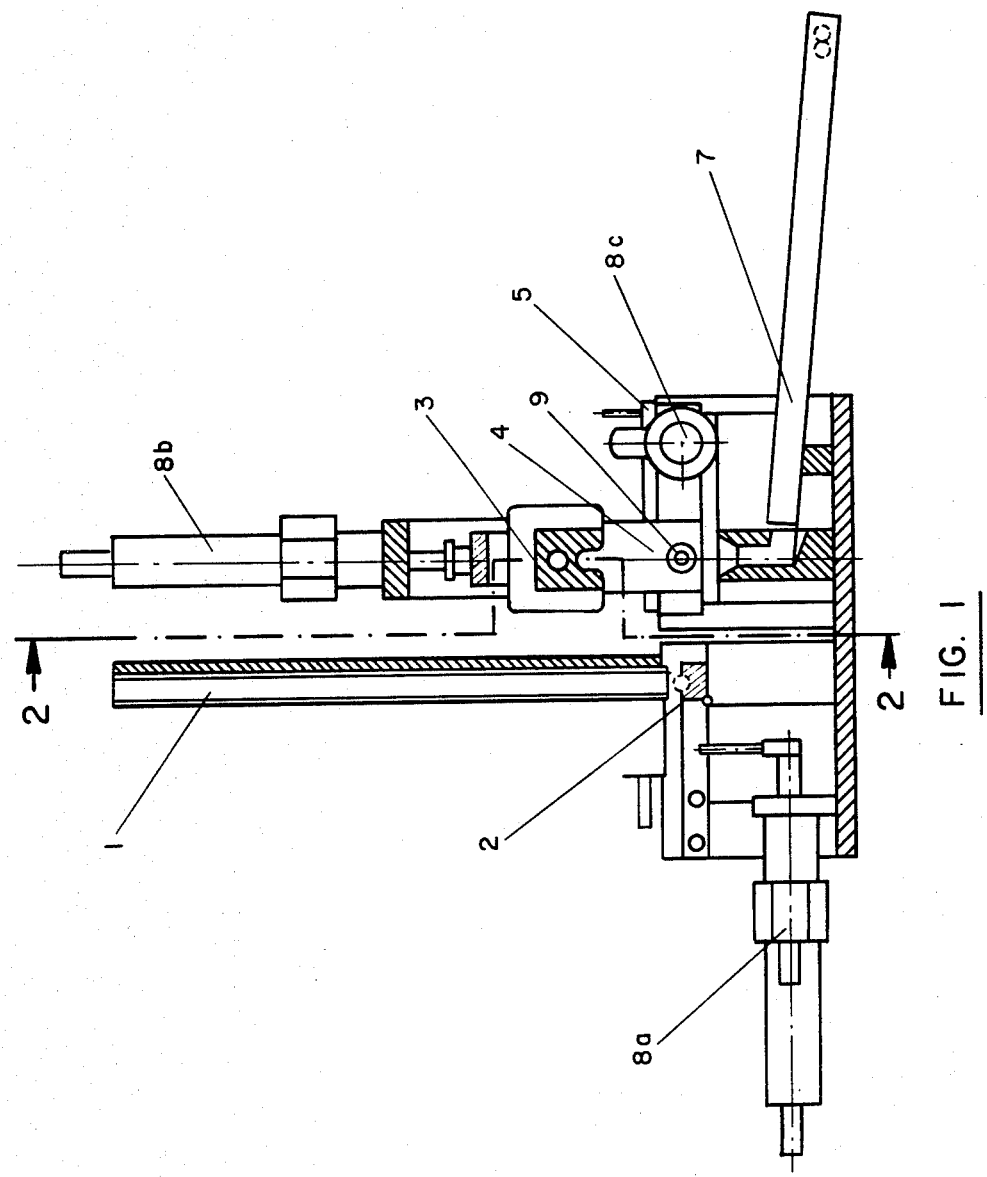

United States Patent [19]

Ellgehausen et al.

[11] Patent Number: 4,470,315
[45] Date of Patent: Sep. 11, 1984

[54] APPARATUS FOR AUTOMATICALLY EXCHANGING SAMPLE TUBES

[75] Inventors: Dieter Ellgehausen; Urs Vögeli, both of Allschwil, Switzerland

[73] Assignee: Sandoz Ltd., Basel, Switzerland

[21] Appl. No.: 386,006

[22] Filed: Jun. 7, 1982

[30] Foreign Application Priority Data

Jun. 11, 1981 [DE] Fed. Rep. of Germany ....... 3123071

[51] Int. Cl.$^3$ .............................................. G01N 1/20
[52] U.S. Cl. .............................. 73/863.12; 73/863.21; 73/864.84
[58] Field of Search ........... 73/864.84, 864.85, 863.11, 73/863.12, 23

[56] References Cited

U.S. PATENT DOCUMENTS

| 3,053,007 | 9/1962 | Tracht | 73/23.1 |
| 3,902,372 | 9/1975 | MacKinnon | 73/864.85 |
| 4,084,440 | 4/1978 | Carpenter | 73/863.11 |
| 4,170,901 | 10/1979 | Conkle et al. | 73/863.12 |

Primary Examiner—S. Clement Swisher

Attorney, Agent, or Firm—Gerald D. Sharkin; Robert S. Honor; Walter F. Jewell

[57] ABSTRACT

An apparatus for introducing tubes automatically into a gas pathway between a gas source and a gas chromatograph when the apparatus is in use, the apparatus comprising a gravity feed magazine for storing tubes, means for introducing a tube horizontally from the magazine to a gas pathway whereby, when the apparatus is in use, gas is introduced through a first pipe from a gas source to one end of the tube and is passed through the tube to a second pipe for introducing the gas into a gas chromatograph, one end of the tube and one end of the first pipe abutting opposite sides of a first resilient ring and the other end of the tube and one end of the second pipe abutting opposite sides of a second resilient ring the rings sealing the first pipe, tube and second pipe in the gas pathway while allowing gas to flow from the first pipe to the tube and from the tube to the second pipe.

means for heating the tube when in the gas pathway and means for ejecting the tube from the pathway.

6 Claims, 2 Drawing Figures

APPARATUS FOR AUTOMATICALLY EXCHANGING SAMPLE TUBES

Small tubes filled or lined with absorbent material are used for analysing adsorbable residual components of a gas (particularly in the analysis of air in pollution studies).

The gas to be tested is passed through or diffuses into a small tube where the residual components, e.g. organic solvent vapours, are deposited on the adsorbent material. For analysis the tube is then placed in the pathway of an elution gas, and as the gas is passed through the tube, the tube is heated in order to release the adsorbed residual components into the elution gas which then passes into a gas chromatograph. When analysing a large number of tubes, for example those resulting from regular studies made in large laboratories and factories, it is impractical to introduce tubes into the gas elution pathway manually as is often the practice.

The invention provides an apparatus for introducing tubes automatically into a gas pathway between a gas source and a gas chromatograph when the apparatus is in use, the apparatus comprising a gravity-feed magazine for storing tubes, means for introducing a tube horizontally from the magazine to a gas pathway whereby, when the apparatus is in use, gas is introduced through a first pipe from a gas source to one end of the tube and is passed through the tube to a second pipe for introducing gas to a gas chromatograph, one end of the tube and one end of the first pipe abutting opposite sides of a first resilient ring and the other end of the tube and one end of the second pipe abutting opposite sides of a second resilient ring; the rings sealing the first pipe, the tube and the second pipe in the gas pathway whilst allowing gas to flow the first pipe to the tube and from the tube to the second pipe, means for heating the tube when in the gas pathway and means for ejecting the tube from the gas pathway.

Preferably the first and second resilient rings are made of natural or synthetic rubber.

Perferably the tubes contain absorbent material within the tubes or lining the inner wall.

Preferably the pipes and the ends of the tubes to which each pipe is connected are of the same diameter.

One advantage of an apparatus according to the invention is that a cheap and reliable mechanism can be produced which allows the analysis of a plurality of tubes without the need for human intervention in the analysis procedure.

Further, according to the invention there is provided a gas chromatograph assembly comprising an apparatus according to the invention as described above, for introducing tubes automatically into a gas pathway, and a chromatograph, the chromatograph being connected to the other end of the second pipe and the assembly having means for displacing the tube being tested from the apparatus and introducing a new tube into the gas pathway in response to a signal from the gas chromatograph.

Preferably a cold trap to concentrate the dose of adsorbed material being introduced onto the column is located between the second pipe and the column of the gas chromatograph of a gas chromatograph assembly of the invention. Such an assembly operates by heating the tube to be tested to a temperature to release the adsorbed material into an elution gas which is a allowed to flow through the tube to the cold trap where the adsorbed material is condensed. In this way the adsorbed material is concentrated and by rapidly heating the cold trap (i.e. in the region of 1000° C. per min.) to a controlled temperature a more concentrated dose of adsorbed material is released from the cold trap on to the column.

Further, the invention provides a method of analysing adsorbed residual components of a gas in a gas chromatograph comprising transferring a tube horizontally from a gravity-feed magazine automatically to a gas pathway, sealing the tube in the gas pathway by contacting one end of a first pipe and one end of the tube to opposite sides of a first resilient ring and contacting the other end of the tube and one end of the second pipe to opposite sides of a second resilient ring whereby the rings seal the first pipe, tube and second pipe in the gas pathway whilst allowing gas to flow from the first pipe to the tube and from the tube to the second pipe, introducing elution gas into the tube, passing it through the tube to the gas chromatograph whilst heating the tube, analysing the gas in the gas chromatograph and ejecting the tube on termination of the elution gas flow in response to a signal from the gas chromatograph.

Figure 2:
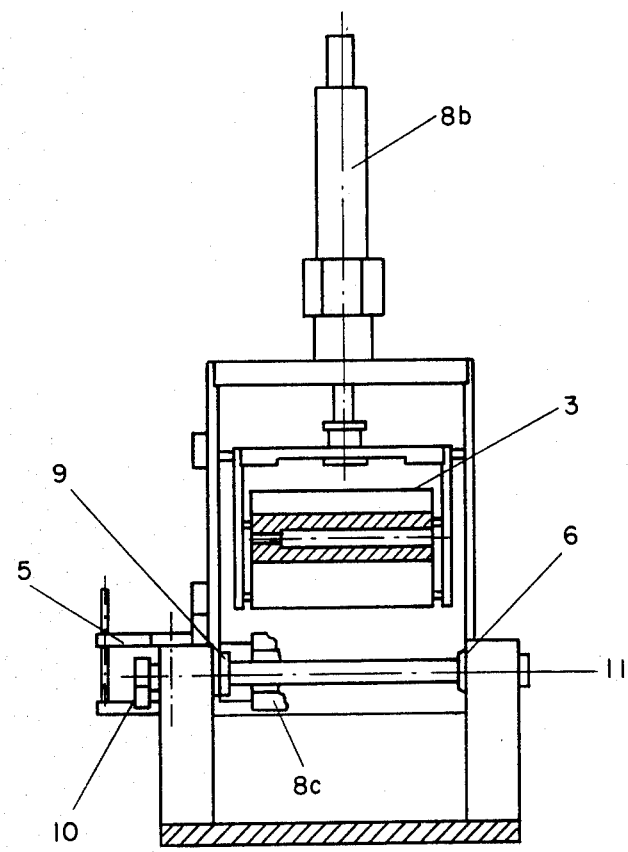

The invention will now be illustrated by way of example only with reference to the accompanying drawings in which FIG. 1 is a cross section of an apparatus according to the invention, and FIG. 2 is a section along A—A of FIG. 1.

FIG. 1 shows an apparatus according to the invention having a magazine 1 for storing sample tubes through which gas is to be passed. Transport means 2 moves a tube from the magazine 1 to position 4 in a gas pathway between a gas source and a gas chromatograph (not shown). Means 2 is operated by a pneumatic piston and cylinder assembly 8a. The tube which is moved to position 4 is held in that position by resting in the groove of a block 5, the groove being of substantially the same radius as the tube. Block 5 is moved in response to activation of piston and cylinder assembly 8c. The tube when in position may be heated by a heater 3 which is brought into the vicinity of the tube in position 4 by a piston and cylinder assembly 8b.

Sealing rings 6 and 9 seal the tube when in position 4 in the gas pathway between a first pipe 10 (for introducing gas from a source into the tube) and a second pipe (for introducing gas from the tube into the gas chromatograph).

In alternative embodiments the pneumatic piston and cylinder assemblies 8a, 8b and 8c may be replaced by electromagnetic parts. Further, the apparatus may contain an injection port before sealing ring 9 in the gas pathway between the gas source and gas chromatograph, the port being for injecting standard gases against which the elution gas may be measured.

When elution is complete, block 5 is moved back into its original position, thereby releasing the tube, which falls into the collection magazine 7.

What is claimed is:

1. An apparatus for introducing tubes automatically into a gas pathway between a gas source and a gas chromatograph when the apparatus is in use, the apparatus comprising a gravity feed magazine for storing tubes, retractable transport means for introducing a tube horizontally from the magazine to a gas pathway whereby, when the apparatus is in use, gas is introduced through a first pipe from a gas source to one end of the tube and is passed through the tube to a second pipe for introducing the gas into a gas chromatograph, one end of the tube and one end of the first pipe abutting opposite sides of a first resilient ring and the other end of the tube and one end of the second pipe abutting opposite sides of a second resilient ring the rings sealing the first pipe, tube and second pipe in the gas pathway whilst allowing gas to flow from the first pipe to the tube and from the tube to the second pipe, heating means substantially surrounding the tube when in the gas pathway, the heating means spaced apart from and in heat isolation from the feed magazine, and means for ejecting the tube from the pathway.

2. An apparatus as claimed in claim 1 in which the both rings are made of rubber.

3. A gas chromatograph assembly comprising an apparatus according to claim 1 and a chromatograph, the chromatograph being connected to the second pipe and having means for displacing the tube being tested from the apparatus and introducing another tube in response to a signal from the gas chromatograph.

4. A gas chromatograph assembly as claimed in claim 3 including a cold trap for concentrating the dose of adsorbed material being introduced onto the column of the gas chromatograph located between the second pipe and the column.

5. A method for analysing adsorbed residual components of a gas in a gas chromatograph comprising transferring a tube horizontally from a gravity-feed magazine automatically to a gas pathway, sealing the tube in the gas pathway by contacting one end of a first pipe and one end of the tube to opposite sides of a first resilient ring and contacting the other end of the tube and one end of the second pipe to opposite sides of a second resilient ring whereby the rings seal the first pipe, tube and second pipe in the gas pathway whilst allowing gas to flow from the first pipe to the tube and from the tube to the second pipe, introducing elution gas into the tube, passing it through the tube whilst heating the tube to the gas chromatograph analysing the gas in the chromatograph and ejecting the tube on termination of the elution gas flow in response to a signal from the chromatograph.

6. A method as claimed in claim 5 in which the elution gas passes into a cold trap located between the second pipe and the column of the gas chromatograph, so that the adsorbed material of the tubes is condensed in the cold trap and heating the cold trap rapidly to release a more concentrated dose of adsorbed material onto the column of the gas chromatograph.

* * * * *